United States Patent
Kanukurthy et al.

(10) Patent No.: US 10,433,787 B2
(45) Date of Patent: Oct. 8, 2019

(54) SELF-ADMINISTERED TAMPER-EVIDENT DRUG DETECTION

(71) Applicant: 3M INNOVATIVE PROPERTIES COMPANY, St. Paul, MN (US)

(72) Inventors: Kiran S. Kanukurthy, Cottage Grove, MN (US); Matthew D. Moore, Lake Elmo, MN (US); Raj Rajagopal, Woodbury, MN (US); Michael E. Hamerly, Vadnais Heights, MN (US)

(73) Assignee: 3M ELECTRONIC MONITORING LTD, Tel Aviv (IL)

( * ) Notice: Subject to any disclaimer, the term of this patent is extended or adjusted under 35 U.S.C. 154(b) by 156 days.

(21) Appl. No.: 15/324,387

(22) PCT Filed: Jul. 6, 2015

(86) PCT No.: PCT/US2015/039174
§ 371 (c)(1),
(2) Date: Jan. 6, 2017

(87) PCT Pub. No.: WO2016/007401
PCT Pub. Date: Jan. 14, 2016

(65) Prior Publication Data
US 2017/0196504 A1    Jul. 13, 2017

Related U.S. Application Data

(60) Provisional application No. 62/021,269, filed on Jul. 7, 2014.

(51) Int. Cl.
*A61B 5/00*    (2006.01)
*A61B 5/1172*  (2016.01)
(Continued)

(52) U.S. Cl.
CPC .......... *A61B 5/4845* (2013.01); *A61B 5/0077* (2013.01); *A61B 5/02055* (2013.01);
(Continued)

(58) Field of Classification Search
CPC .............. A61B 5/4845; A61B 5/14507; A61B 5/02055; A61B 5/0077; A61B 5/1172;
(Continued)

(56) References Cited

U.S. PATENT DOCUMENTS

| | | | | |
|---|---|---|---|---|
| 4,843,377 A | * | 6/1989 | Fuller | G07C 9/00103 340/573.4 |
| 5,133,935 A | * | 7/1992 | Copelan | A61B 5/1171 422/430 |

(Continued)

FOREIGN PATENT DOCUMENTS

| WO | WO 1992-16842 | 10/1992 |
|---|---|---|
| WO | WO 2000-63696 | 10/2000 |

(Continued)

OTHER PUBLICATIONS

StreetTime Technologies, [Online], [retrieved from the internet on Jan. 24, 2017], URL < http://www.streetimetechnologies.com/PassPoint.html>, 1 page.

(Continued)

*Primary Examiner* — Adnan Aziz
(74) *Attorney, Agent, or Firm* — Soroker Agmon Nordman

(57) ABSTRACT

A self-administered tamper-evident drug detection system. The system includes a biometric detection surface for each of a user's right and left hands, configured to identify the user and prevent tamper by continuously capturing biometric information from each of the user's right and left hands while the system is administering a drug detection test. The system further includes a collection device to administer the (Continued)

drug detection test by exposing a sample collection device to a user's mouth to collect a saliva sample.

20 Claims, 6 Drawing Sheets

(51) Int. Cl.
*A61B 5/0205* (2006.01)
*A61B 10/00* (2006.01)
*A61B 5/145* (2006.01)
*G01N 33/94* (2006.01)
*G06K 9/00* (2006.01)
*A61B 5/024* (2006.01)
*A61B 5/053* (2006.01)
*A61B 5/1171* (2016.01)

(52) U.S. Cl.
CPC ........ *A61B 5/1172* (2013.01); *A61B 5/14507* (2013.01); *A61B 10/0051* (2013.01); *G01N 33/94* (2013.01); *G06K 9/00* (2013.01); *G06K 9/00006* (2013.01); *A61B 5/024* (2013.01); *A61B 5/0533* (2013.01); *A61B 5/1176* (2013.01); *A61B 2010/0003* (2013.01); *A61B 2010/0009* (2013.01)

(58) Field of Classification Search
CPC ..... A61B 5/0533; A61B 5/1176; A61B 5/024; A61B 10/0051; A61B 2010/0003; A61B 2010/0009; G06K 9/00006; G01N 33/94
See application file for complete search history.

(56) References Cited

U.S. PATENT DOCUMENTS

| | | | |
|---|---|---|---|
| 5,223,221 A * | 6/1993 | Copelan | A61B 5/117 600/573 |
| 5,229,764 A | 7/1993 | Matchett | |
| 5,719,950 A | 2/1998 | Osten | |
| 5,817,012 A | 10/1998 | Schoendorfer | |
| 5,876,926 A * | 3/1999 | Beecham | A61B 5/1171 435/5 |
| 6,148,094 A | 11/2000 | Kinsella | |
| 6,372,516 B1 | 4/2002 | Sun | |
| 6,433,863 B1 | 8/2002 | Weiss | |
| 6,748,792 B1 * | 6/2004 | Freund | B60K 28/063 180/272 |
| 6,947,580 B1 | 9/2005 | Kinsella | |
| 6,956,484 B2 * | 10/2005 | Crespo | A61B 5/18 180/272 |
| 6,964,752 B2 * | 11/2005 | Lappe | B01L 3/502 422/82 |
| 7,222,360 B1 | 5/2007 | Miller | |
| 7,616,788 B2 | 11/2009 | Hsieh | |
| 7,741,103 B2 | 6/2010 | Guirguis | |
| 8,830,032 B2 * | 9/2014 | Hamilton, II | G06K 9/00006 340/5.52 |
| 9,922,508 B2 * | 3/2018 | Keays | G08B 1/08 |
| 2002/0089660 A1 | 7/2002 | Weiss | |
| 2002/0095586 A1 | 7/2002 | Doyle | |
| 2002/0146346 A1 | 10/2002 | Konecke | |
| 2003/0064526 A1 | 4/2003 | Niedbala | |
| 2004/0082878 A1 * | 4/2004 | Baldwin | A61B 10/0051 600/573 |
| 2005/0100191 A1 | 5/2005 | Harbach | |
| 2005/0119589 A1 | 6/2005 | Tung | |
| 2005/0177096 A1 * | 8/2005 | Bollish | A61B 5/02055 604/65 |
| 2006/0008920 A1 | 1/2006 | Wong | |
| 2006/0013738 A1 | 1/2006 | Ramsey | |
| 2006/0074280 A1 * | 4/2006 | Martis | A61B 3/005 600/310 |
| 2008/0040780 A1 * | 2/2008 | Reinhold | H04L 63/0861 726/5 |
| 2009/0087920 A1 * | 4/2009 | Pettersson | B60K 28/066 436/132 |
| 2009/0312595 A1 * | 12/2009 | Leuthardt | G06F 19/3481 600/27 |
| 2010/0016754 A1 | 1/2010 | Whillock | |
| 2010/0204600 A1 | 8/2010 | Crucilla | |
| 2011/0144454 A1 | 6/2011 | Koester | |
| 2011/0178420 A1 * | 7/2011 | Ridder | A61B 5/14546 600/532 |
| 2011/0304465 A1 * | 12/2011 | Boult | B60K 28/06 340/576 |
| 2012/0253154 A1 | 10/2012 | Phillips | |
| 2013/0006068 A1 | 1/2013 | Gemer | |
| 2013/0035602 A1 | 2/2013 | Gemer | |
| 2015/0315564 A1 * | 11/2015 | Kindt | A61B 50/00 600/572 |
| 2015/0326570 A1 * | 11/2015 | Publicover | G06F 21/64 726/4 |
| 2015/0356286 A1 * | 12/2015 | Quirk | G06F 21/32 726/19 |

FOREIGN PATENT DOCUMENTS

| | | |
|---|---|---|
| WO | WO 2005-121793 | 12/2005 |
| WO | WO 2008-096225 | 8/2008 |
| WO | WO 2010-106061 | 9/2010 |
| WO | WO 2011-078887 | 6/2011 |
| WO | WO 2012-138663 | 10/2012 |

OTHER PUBLICATIONS

MCJ Eyecheck™ Pupillometer, Barenco Creative Security Solutions, [Online], [retrieved from the internet on Sep. 8, 2017], URL <http://www.barenco.com/security-products/eyecheck-pupillometer.asp>.

International Search Report for PCT International Application No. PCT/US2015/039174 dated Sep. 29, 2015, 8 pages.

* cited by examiner

SELF-ADMINISTERED TAMPER-EVIDENT DRUG DETECTION

CROSS REFERENCE TO RELATED APPLICATIONS

This application is a national stage filing under 35 U.S.C. 371 of PCT/US2015/039174, filed Jul. 6, 2015, which claims the benefit of Provisional Application No. 62/021,269, filed Jul. 7, 2014, the disclosures of each of which are incorporated by reference in its/their entirety herein.

TECHNICAL FIELD

The present disclosure relates to the field of self-administered drug detection systems and methods. More specifically, the present disclosure relates to self-administered drug detection systems that are tamper evident.

BACKGROUND

Drug detection plays an important role in law enforcement or criminal justice, employment and other settings. For example, many companies require new employees to successfully complete drug screening prior to beginning work at a particular place of employment. Some employers require successful drug screening on an ongoing basis.

In aspects of law enforcement and criminal justice, drug or alcohol monitoring or detection systems are used in a variety of contexts. In some contexts, individuals are required to complete drug testing prior to being checked into a prison or other detainment location. In other contexts, individuals who were arrested for violations related to drugs or alcohol, such as driving while inebriated, possession and use of narcotics, or other illegal substances, are required to complete a probationary period after being released from prison or confinement. The probationary period will often have requirements related to the prohibition of drug and alcohol use. Recurrent drug screening or monitoring are often required to enforce the restrictions during the probation period.

While there are a variety of alcohol testing devices available commercially, and fewer available drug-testing systems, in order to reduce cost of administering drug tests, it is important to have a system that can monitor whether or not the individual providing a test sample is the individual being monitored. Improvements in options for self-administered drug-detection systems would be welcomed.

SUMMARY

The present disclosure provides a variety of advantages over existing technical solutions. For example, a device consistent with the present disclosure can be self-administered and does not require supervision by a test administrator or law enforcement official during administration. The present disclosure allows for local analysis and data capture, and transmission to a remote server or storage mechanism, which provides a system that is self-contained, mobile and portable.

In one aspect, the present disclosure includes a self-administered tamper evident drug detection system. The system includes a biometric detection surface, for each of a user's right and left hands, configured to identify the user and prevent tamper by continuously capturing biometric information from each of the user's right and left hands while the system is administering a drug detection test. The system further includes a collection device to administer the drug detection test by exposing a sample collection device to a user's mouth to collect a saliva sample.

In another aspect, the present disclosure includes a method of administering a drug detection test. The method includes providing a self-administered tamper-evident drug detection system, the system comprising a biometric detection surface for each of a user's right and left hands and a collection device. The method further includes requiring a user to place each of their right and left hands on the biometric detection surfaces and continuously capturing biometric information from each of the user's right and left hands. The method also includes administering a drug detection test by exposing a sample collection device to a user's mouth to collect a saliva sample while the biometric information is being continuously captured.

BRIEF DESCRIPTION OF DRAWINGS

The following figures provide illustrations of the present disclosure. They are intended to further describe and clarify the disclosure, but not to limit the scope of the disclosure to the illustrated configurations.

Like numbers are generally used to refer to like components. The figures are not to scale and are for illustrative purposes only.

DETAILED DESCRIPTION

Figure 1:
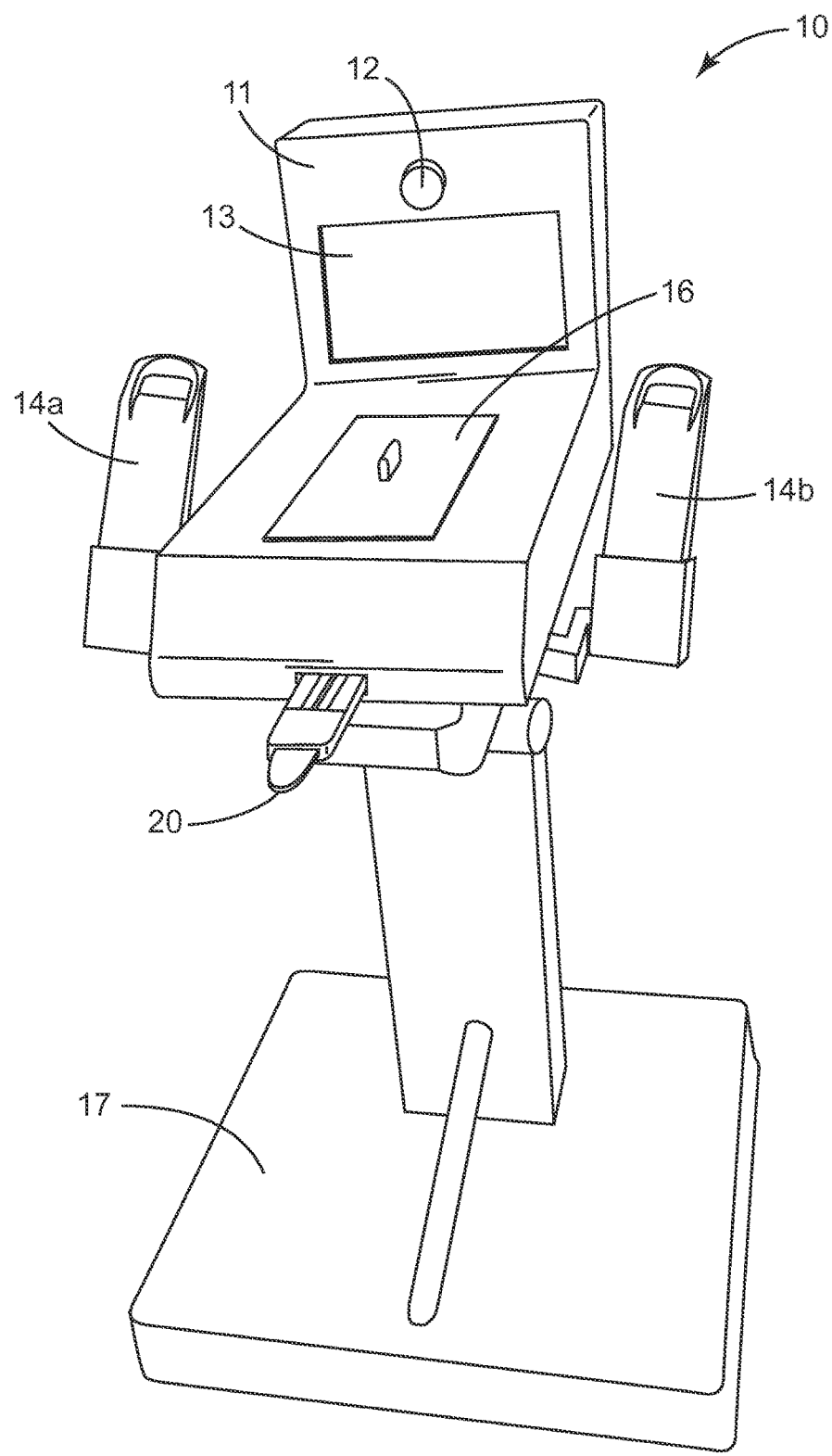
FIG. 1 is an exemplary self-administered tamper-evident drug detection system.

FIG. 1 is an exemplary self-administered tamper-evident drug detection system 10. System 10 includes a biometric detection surface 14a, 14b for each of user's right and left hands, housing 11, camera 12, display 13, collection device mechanism 16, collection device 20 and stand 17.

In some configurations, housing 11 contains biometric detection surfaces 14a, 14b, camera 12, display 13, collection device mechanism 16, collection device 20 and stand 17 in a single, self-supporting structure. This allows system 10 to be portable and easily relocated and used in a variety of locations and contexts.

Camera 12 can be used to capture or record an image of the user's face while the system is administering the drug detection test. In some configurations, the image of the user's face can be used to confirm the user's identity. In other configurations, the image of the user's face can be stored and used as a secondary indicator of tamper if the biometric detection surfaces show any primary tamper indication. Camera 12 may be Charge Coupled Device (CCD) or Complementary Metal-Oxide Semiconductor (CMOS) varieties, color sensing devices or the like.

Display 13 can be used to display a variety of information. It can be used to provide step by step instructions to a user during a registration process. Display 13 can display instructions to guide a user through a drug detection testing process. Additionally, display 13 can be used to display the image collected by camera 12 so that a user completing a drug detection is able to see the image that is captured and associated with that particular test. Display 13 may be Liquid Crystal Display (LCD), Light Emitting Diode (LED), Plasma Display Panel (PDP), Digital Light Projection (DLP) varieties, quantum dot, OLED, bi-stable displays or the like.

The biometric detection surfaces 14a, 14b can include a pad on which a user can place a thumb, finger or hand. The system 10 then captures biometric identification information, such as the fingerprint, handprint or vein pattern associated with each of the right and left fingers or hands placed on biometric detection surfaces 14a, 14b. Additional biometric information that can be captured by biometric detection surfaces 14a, 14b includes, for example, galvanic skin response, skin conductivity, pulse and temperature.

System 10 can be configured to continuously capture biometric information. The information may be captured at a range of rates, such as one sample per second, ten samples per second, 100 samples per second, or any rate in-between or higher.

System 10, through biometric detection surfaces 14a, 14b may continuously capture biometric information during a single or multiple sample periods. For example, the information may be captured before the user begins to provide a saliva sample to the device, during the time that the user provides a saliva sample to the device, after the completion of the saliva sample collection or during any other sample period or combination of sample periods.

A user's palm, finger or thumb can be placed on the surface 14a and 14b. The captured print can be compared with a print stored in the system 10 or stored remotely and associated with a particular user. The biometric detection surfaces 14a, 14b can be configured to identify the user and prevent tamper by continuously capturing biometric information from each of the user's right and left hands while the system 10 is administering a drug detection test.

Biometric information captured by system 10 can be used to confirm a user's identity based on pre-registered information for the user.

System 10 further includes a collection device 20 to administer the drug detection test by exposing a sample collection device 20 to a user's mouth to collect a saliva sample. Collection device 20 can be normally housed within housing 11 of system 10 such that a collection device is exposed to a user during a time period where a user is instructed or intended to provide a saliva sample. After the time period or collection of the saliva sample, collection device 20 can be withdrawn into system 10 to be tested for indications of drugs or illegal substances. Collection device 20 may be a strip, a vacuum pump or a breath collection device.

Collection device mechanism 16 can store multiple collection devices 20 such that the machine can perform multiple drug detection tests for a single or multiple individuals and store the used collection devices until system 10 is restocked. System 10 can be periodically restocked so that used collection devices 20 are removed and the stock of collection devices 20 in system 10 is replenished.

System 10 may also include an integrated processing component configured to confirm the user's identity during a time period over which biometric information is continuously collected and to analyze the saliva sample for the presence of drugs. An integrated processing component may also be configured to only confirm the user's identity based on an initial sample or shortened sample period, and after confirming identity based on initial sample period, the processing component may then detect a continuous sample, such that the collected biometric information does not change beyond predefined parameters during the remainder of the sample period.

A user's identity can be confirmed based on pre-registered information for the user, such that there is a match between stored identification information associated with the user and the identification information collected by system 10. Identification information can be stored locally on system 10 or remotely on a remote server or processor.

Figure 2:
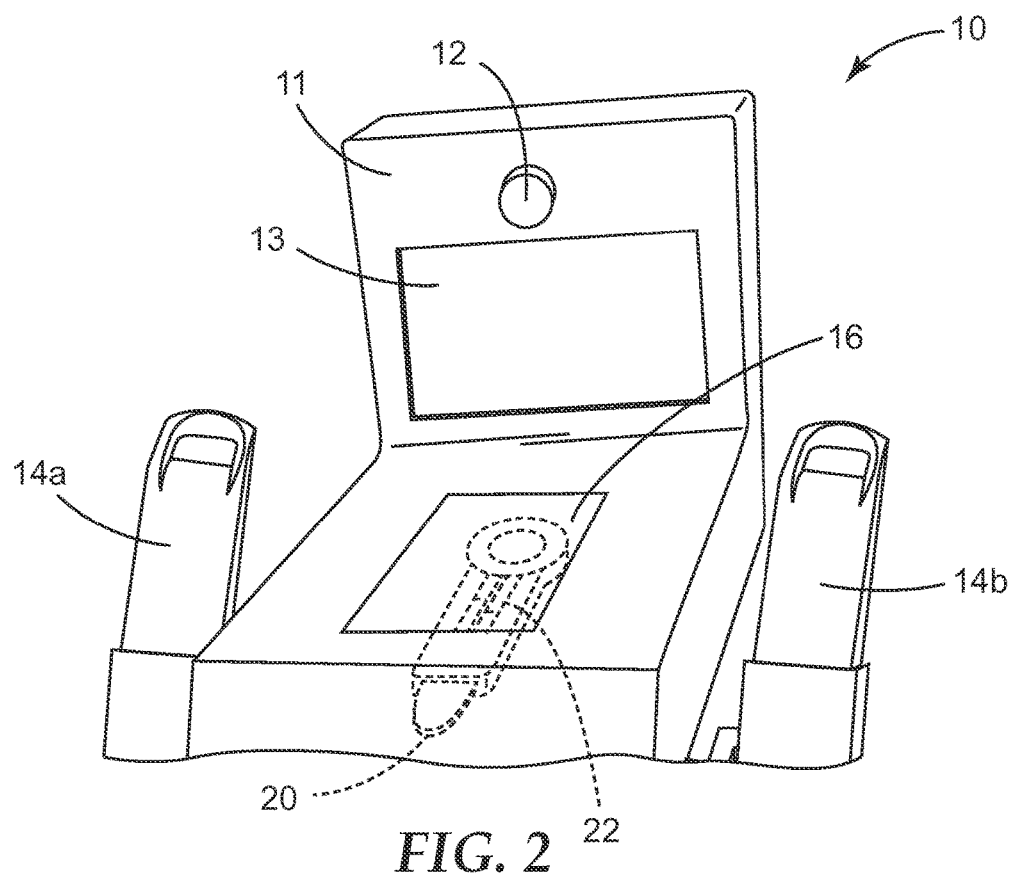
FIG. 2 is an exemplary self-administered tamper-evident drug detection system showing a sample collection device.

FIG. 2 is an exemplary self-administered tamper-evident drug detection system 10 showing a sample collection device mechanism 16. System 10 includes a biometric detection surface 14a, 14b for each of user's right and left hands, housing 11, camera 12, display 13, and collection device mechanism 16. As shown in FIG. 2, collection device mechanism 16 can be accessed through an opening created by removing an exterior portion of housing 11. Collection device mechanism 16 can store a cartridge 22 of individual collection devices 20 that can be exposed to a user by ejecting the collection device 20 through an opening in housing 11. Collection device mechanism 16 can then mechanically retract the individual collection device to perform an initial test on the saliva collected by the individual collection device.

In some configurations where a strip is used as a collection device, each strip may be preprinted with a unique barcode to allow tracking of samples collected and further analysis of specific samples if required.

Figure 3:
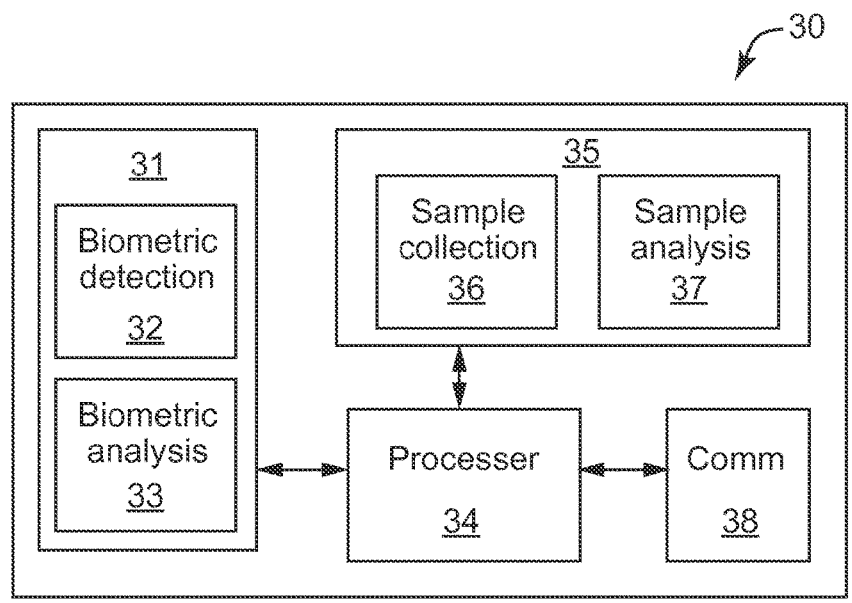
FIG. 3 is a block diagram of components within a tamper-evident drug-detection system.

FIG. 3 is a block diagram of components within a tamper-evident drug-detection system 30. System 30 includes a number of components, including biometric unit 31, sample unit 35, processor 34 and communication unit 38. Biometric unit 31 includes a biometric detection device 32 and biometric analysis device 33. Biometric detection device 32 collects identifying biometric information from a user. For example, biometric detection device 32 may collect identifying biometric information such as a vein pattern, palm or finger print. It may also collect information such as temperature, pulse and liveness. Biometric analysis device 33 can analyze the identifying biometric information collected. Analysis can include matching for purposes of identification, verification of liveness, and/or sensing of anomalies in any of the detected items.

Sample unit 35 includes sample collection device 36 and sample analysis 37. Sample collection device 36 can be a variety of devices including a collection material attached to lateral flow strips, swab, pump or any other desired devices. Sample analysis device 37 analyzes the collected sample. The analysis performed by sample analysis device 37 can be either a preliminary or final analysis. For example, sample analysis device 37 may analyze whether there are any prohibited substance indicators in the collected sample. If there are prohibited substance indicators, then the collected sample may be subjected to further analysis inside system 30 or may be analyzed further externally.

Processor 34 controls system 30. It can store information related to individuals who are registered to use system 30, such as a user profile. A user profile may include information such as reference facial scans, finger or palm prints, vein patterns, previous drug test results, baseline pulse and temperature data and contact or other demographic information for the user. Processor 34 also controls sample unit 35 and biometric unit 31, and may perform the processing required by sample unit 35 or biometric unit 31. Processor 34 can authenticate identification based on facial scans or biometric identification information. Processor 34 can perform an enrollment process for a new user. Processor 34 can communicate with an external system or server via communication unit 38. Processor may be configured to send an alarm to an external system based on input from tamper evident intrusion devices in the system. Communication unit 38 may enable a variety of types of communication including wired and wireless connections, including WiFi, Bluetooth, cellular, or through a traditional landline connection.

Figure 4:
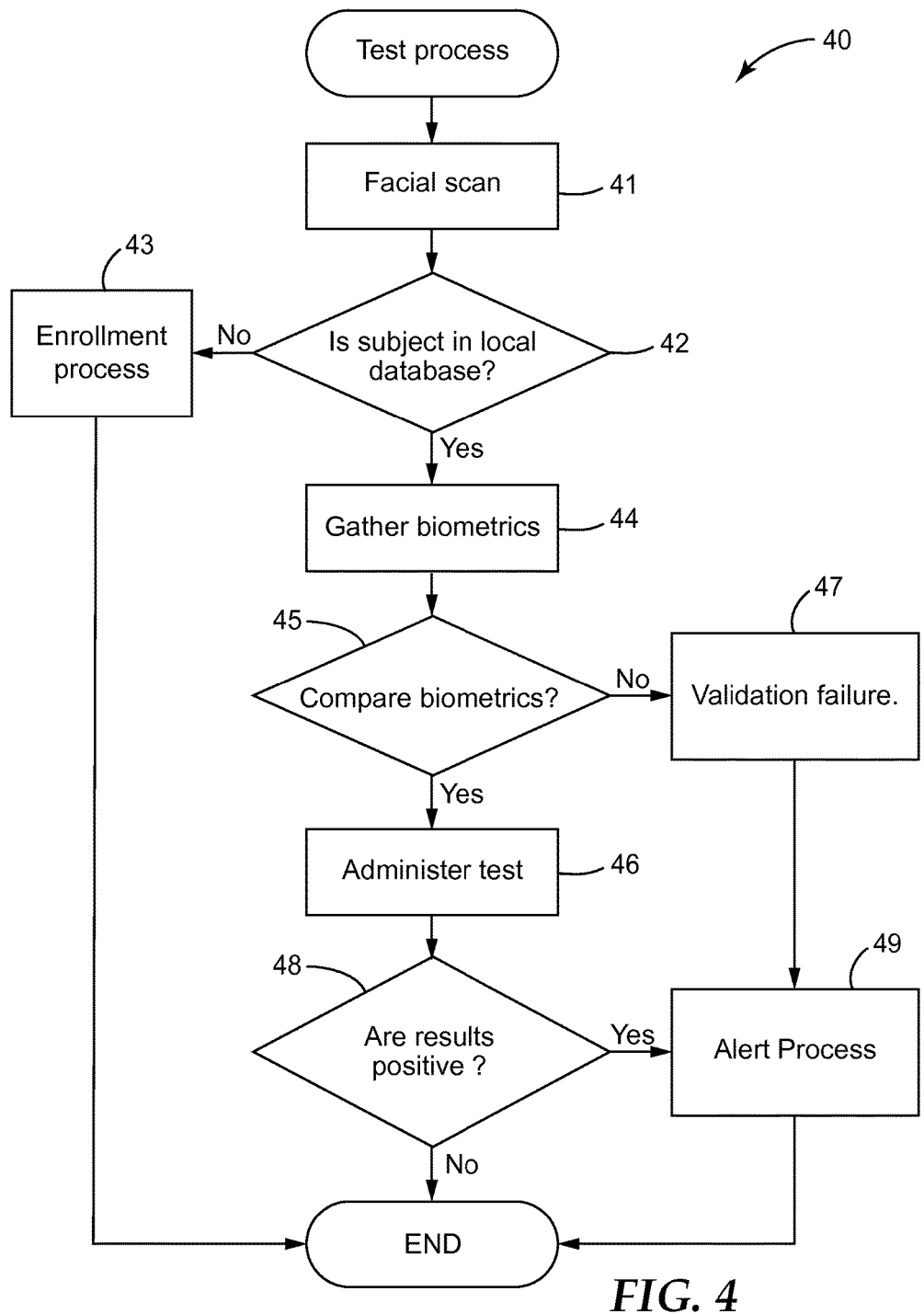
FIG. 4 is a flow chart illustrating a test process for the drug detection system.

FIG. 4 is a flow chart 40 illustrating a test process for the drug detection system. While the test process shown is one exemplary process for a system consistent with the present disclosure to perform, a variety of other processes or a modification of the described process are within the scope of the present invention and will be apparent to one of skill in the art upon reading the present disclosure. Test process 40 begins with facial scan 41. Facial scan 41 can be conducted by a camera as shown in FIG. 1. After the facial scan 41 is complete, the system determines whether the subject is in the local database 42 by comparing and matching the facial scan to any stored image. In step 42, if the subject is not in the local database, the system launches an enrollment process 43. The enrollment process 43 results in an invalidated test result.

If the subject is in the local database, then in step 44, the device gathers biometric information, including identifying biometric information. In some instances, this may be vein patterns, fingerprints or palm prints.

In step 45, the system compares the collected identifying biometric information, such as a fingerprints or palm prints, and to locally stored biometric information of the same type. If the collected and stored biometric information do not match, the system registers a validation failure in step 47. In the case of a validation failure due to a mismatch of collected and stored identifying biometric information, the system initiates an alert process in step 49. The alert process includes providing a local alert to the subject, including an audible or visible alert, and providing a remote alert by wired or wireless means to a remote server or other responsible individual such as a parole officer.

If the collected and stored biometric information do match in step 45, the system then administers the test in step 46. Administering the test is discussed in greater detail in FIG. 5. If the results of the test are positive, the user may be instructed or required to complete additional testing at another location, such as at a drug testing agency. In other instances, the user may be instructed to complete a second test with the system. The system may also initiate the alert process in step 49. If the results of the test are not positive, the system completes or ends the test. The system also ends the test upon completion of the alert process in step 49. After the test is completed, the user profile may be updated and results are transmitted back to an external system. In some instances, the results may be displayed to the user.

Figure 5:
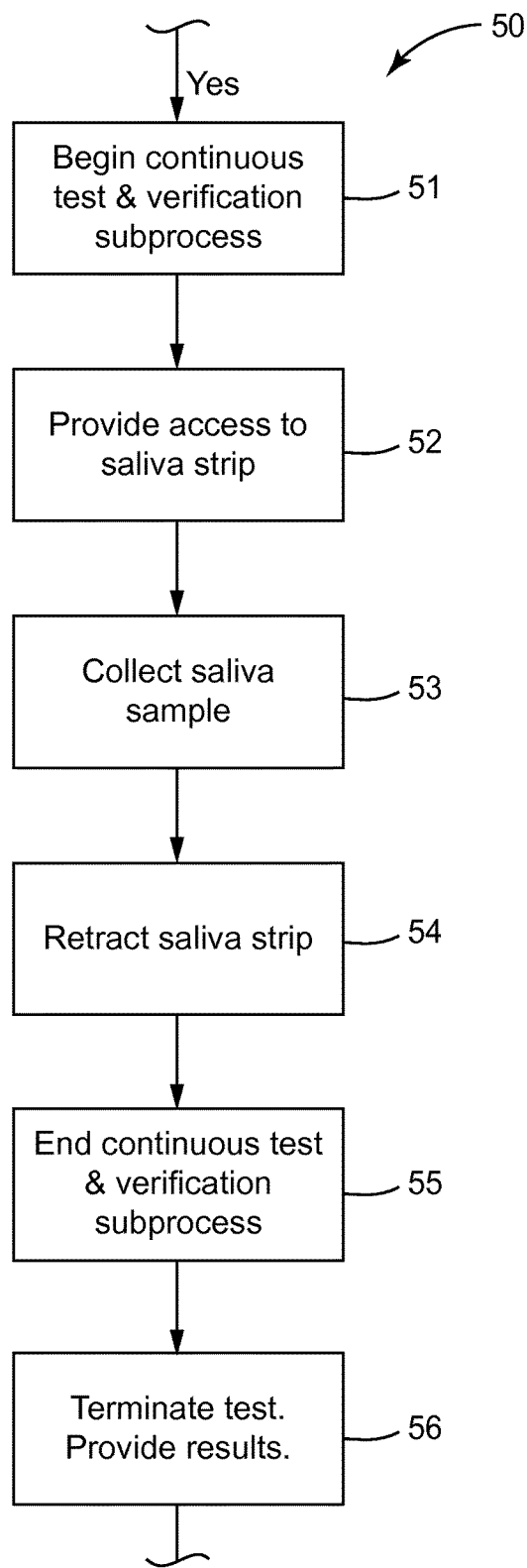
FIG. 5 is a flow chart illustrating the steps of administering a test.

FIG. 5 is a flow chart 50 illustrating the steps of administering a test as mentioned in step 46 in FIG. 4. In step 51, the system begins a continuous test and verification subprocess. While the subprocess in step 51 is running, the system moves to step 52 where it provides access to a saliva strip to a user. The system does this by exposing a portion of the saliva strip to the user while the strip is being secured in place by the system. A user cannot pick up or move the strip because their hands are required to be in contact with the biometric detection surfaces during the test. After access to a saliva strip is provided to a user, the systems collects a saliva sample by receiving a sample deposited on the strip by a user by the user placing their mouth over the strip, and most preferably placing the strip under their tongue. The display can instruct the user in the steps of providing a sample. In some instances, the user may have to leave the strip in their mouth for a minimum period of time. The period of time can be displayed by the display to provide guidance to the user. In another configuration, the device may use sensors to determine when sufficient saliva has been collected for testing, and the user may be notified that they may release the strip from their mouth when enough saliva has been collected. In step 54, the system retracts the saliva strip. This ends a user's access to the saliva strip by containing the strip within the system. After the strip is retracted, in step 55, the system ends the continuous test and verification subprocess. The continuous test and verification subprocess is running during the entire time the saliva strip is exposed to a user. In step 56, the system terminates the test and provides results. The results are provided to the system processor, which then queries whether the results are positive, as described in step 48 of FIG. 4.

The saliva sample may be analyzed to produce results through a variety of methods. These methods include configurations such as sensing the presence of a drug or drug metabolite using a chemical reaction colorimetrically, fluorimetrically, luminetrically, or a combination thereof. The presence of drugs may also be identified by sensing the presence of the drug or drug metabolite coupled to a compound having an affinity to the drug. More specifically, the system may sense the presence of the drug or a drug metabolite coupled to a compound by an antigen-antibody interaction. In some configurations, the antigen-antibody interaction may be an immunoassay. In some configurations, the system may sense the presence of at least two different drugs in the saliva. And in other instances, a lateral flow device may be used to collect saliva and a sensor for sensing the presence of drugs or alcohol may be part of the lateral flow device. Details of drug detection are discussed, for example, US Published Patent Application 20130006068, incorporated herein by reference.

While FIG. 5 shows a particular sequence of steps for administering the test based on use of a saliva strip to collect a saliva sample, other types of collection devices and variations in the process described in FIG. 5 are within the scope of the present disclosure and will be apparent to an individual of skill in the art upon reading the present disclosure.

Figure 6:
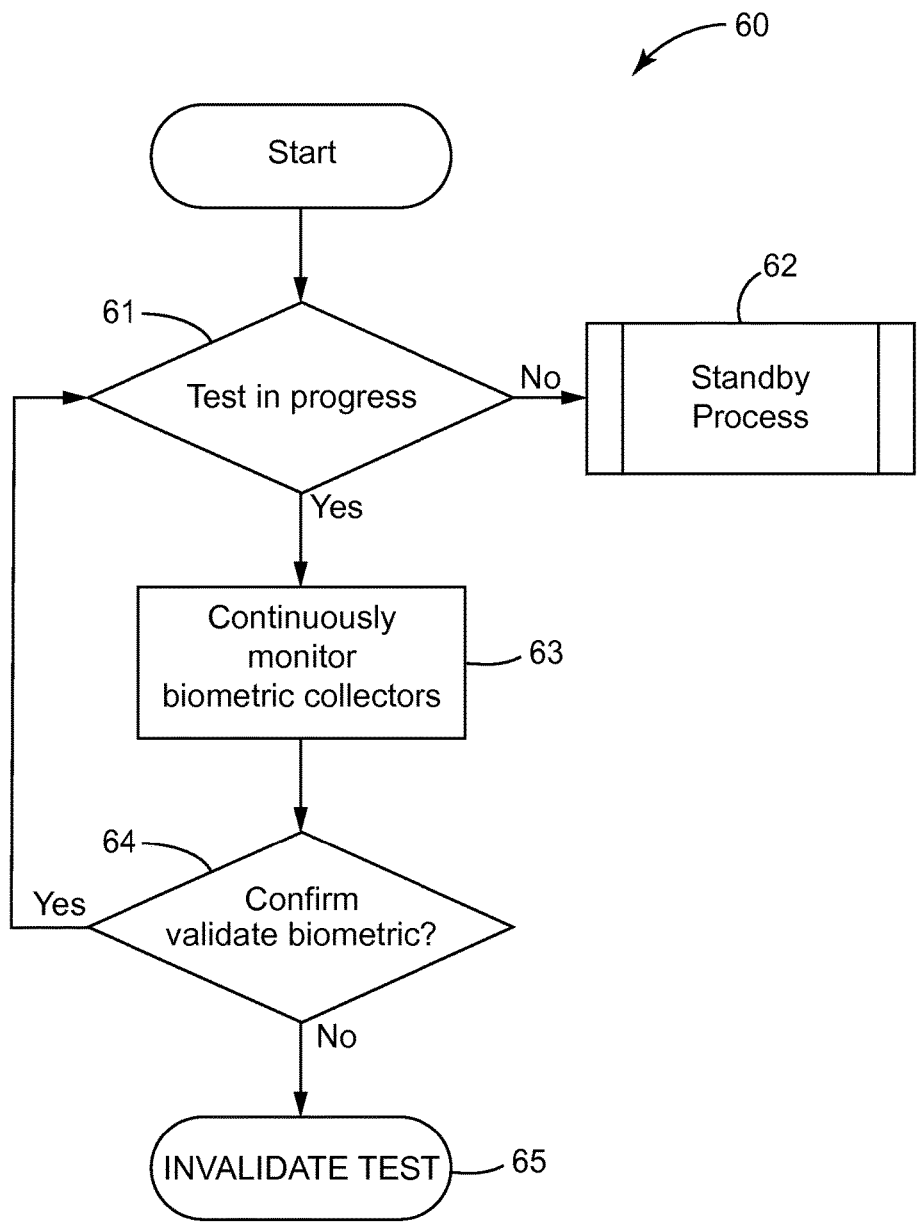
FIG. 6 is a flow chart illustrating a continuous biometrics validation process.

FIG. 6 is a flow chart 60 illustrating a continuous biometrics validation process that can be used for verifying identity through fingerprints or palm prints. In step 61, the system determines whether a test is in progress. If there is no test in progress, the system reverts to a standby process as shown in step 62 and illustrated in further detail in FIG. 7. If there is a test in progress, the system moves to step 63, where it begins to continuously capture biometric information from both biometric detection surfaces. Continuously capturing information includes sampling the biometric information. Details of a technique to capture and compare biometric information are described, for example, in U.S. Pat. No. 7,616,788 to Hsieh et al incorporated herein by reference. The sampling rate may vary depending on the configuration, but may be in the range of 10-100 samples per second. The continuous monitoring of both biometric detection surfaces ensures that a user must maintain contact between both hands and these surfaces. This prevents a user from using their hands to tamper or otherwise alter or substitute the saliva sample or test results.

After the system begins continuously monitoring both biometric detection surfaces in step 63, the system validates the detected biometrics in step 64. Validating the biometrics can include a variety of checks, including confirming that the user's fingers or palms are present without a discontinuity on either biometric detection surface. It can include checking to see if there is an abnormality in the image frames. It can monitor for anomaly in temperature, pulse and liveness. It can also include other checks to ensure that the biometric information detected on the reader and used to confirm a user's identity has not changed.

In the case that the biometrics are validated in step 64, and the test is still in progress, the system loops to continuously monitor and validate the biometrics. In the case that the biometrics are not validated in step 64, the system invalidates the current test in step 65.

Figure 7:
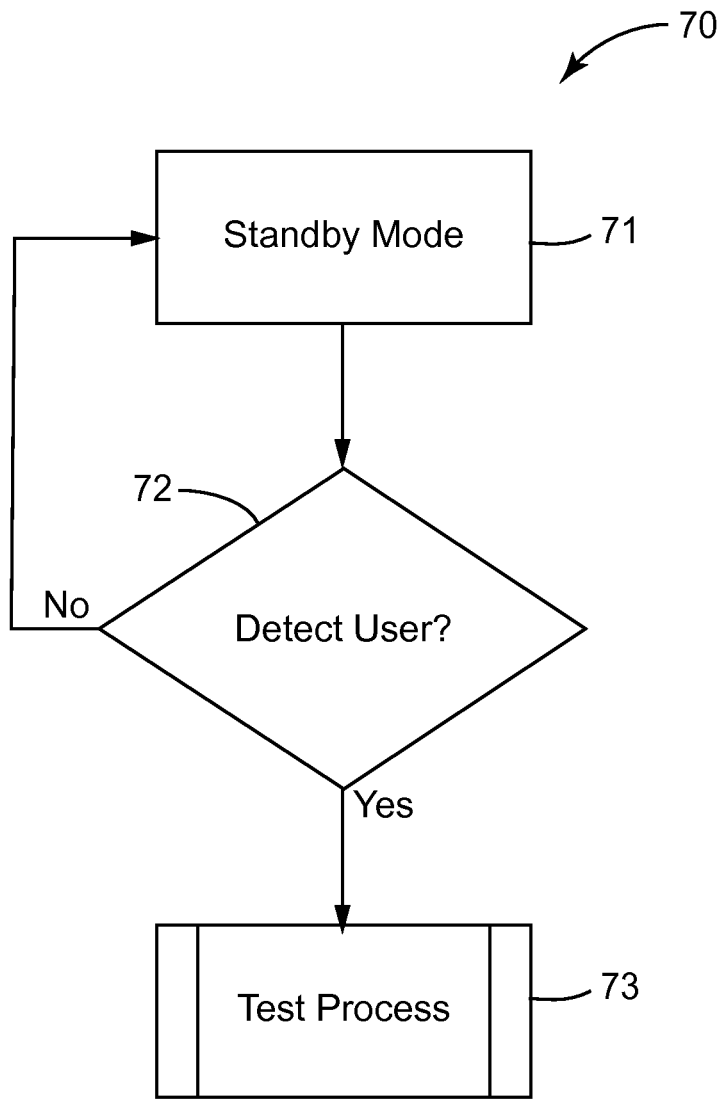
FIG. 7 is a flow chart illustrating a standby process prior to beginning the test process.

FIG. 7 is a flow chart 70 illustrating a standby process prior to beginning the test process. When the system is in a standby mode 71 during the standby process as shown in step 62 in FIG. 6, the system checks to see whether it detects the presence of a user by detecting a finger or palm on the biometric detection surface in step 72. If no finger or palm is detected, the system reverts to standby mode 71 where it periodically makes the same check. If a finger or palm is detected, the system enters the test process 73. The test process is shown in further detail in FIG. 4.

The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Variations on the present disclosure will be apparent to one of skill in the art upon reading the present disclosure, and are intended to be included within the scope of the present disclosure. For example, a variety of electronic components may be used as a controlled switching module or microcontroller.

What is claimed is:

1. A self-administered tamper-evident drug detection system comprising:
    a biometric detection surface for each of a user's right and left hands, configured to identify the user and prevent tamper by continuously capturing biometric information from each of the user's right and left hands while the system is administering a drug detection test;
    a collection device to administer the drug detection test by exposing a sample collection device to the user's mouth to collect a saliva sample while the biometric information is being continuously captured;
    wherein the system invalidates the drug detection test if the biometric information is not continuously validated throughout the entire drug detection test;
    wherein the collection device is provided as a replaceable cartridge with multiple sample collection devices and a single sample collection device is exposed to the user for a period of time for testing and then mechanically retracted into the collection device for analysis; and
    wherein the system includes a display that guides the user as to when to release the sample collection device from the user's mouth.

2. The drug detection system of claim 1, wherein the system is contained in a single housing.

3. The drug detection system of claim 1, wherein the continuously captured biometric information is captured at a rate of 10-100 samples per second.

4. The drug detection system of claim 1, wherein the biometric information is biometric identification information.

5. The drug detection system of claim 4, wherein the biometric identification information includes at least one of: a fingerprint, a handprint, and a vein pattern.

6. The drug detection system of claim 1, wherein the biometric information includes at least one of a galvanic skin response and skin conductivity.

7. The drug detection system of claim 1, further comprising a camera to record an image of the user's face while the system is administering the drug detection test.

8. The drug detection system of claim 1, further comprising an integrated processing component configured to confirm the user's identity during a sample time period and to analyze the saliva sample for the presence of drugs.

9. The drug detection system of claim 1, wherein the biometric detection surface continuously captures biometric information during two sample periods.

10. The drug detection system of claim 1, wherein the sample collection device is at least one of a strip, a vacuum pump, and a breath collection device.

11. The drug detection system of claim 1, wherein the user's identity is confirmed based on pre-registered information for the user.

12. The drug detection system of claim 1, wherein each sample collection device is preprinted with a unique barcode for tracking during further analysis.

13. A method of administering a drug detection test comprising:
providing a self-administered tamper-evident drug detection system, the system comprising a biometric detection surface for each of a user's right and left hands and a collection device;
requiring a user to place both the right hand and the left hand on the biometric detection surfaces and continuously capturing biometric information from each of the user's right and left hands;
administering a drug detection test by exposing a sample collection device to the user's mouth to collect a saliva sample while the biometric information is being continuously captured;
wherein the system invalidates the drum detection test if the biometric information is not continuously validated throughout the entire drug detection test;
wherein the collection device is provided as a replaceable cartridge with multiple sample collection devices and a single sample collection device is exposed to the user for a period of time for testing and then mechanically retracted into the collection device for analysis; and
wherein the system includes a display that guides the user as to when to release the sample collection device from the user's mouth.

14. The method of claim 13, wherein the biometric information is biometric identification information.

15. The method of claim 14, wherein the biometric identification information includes at least one of: a fingerprint, a handprint, and a vein pattern.

16. The method of claim 13, wherein the biometric information includes at least one of a galvanic skin response and skin conductivity.

17. The method of claim 13, further comprising recording an image of the user's face while administering the drug detection test.

18. The method of claim 13, further comprising confirming the user's identity during a sample time period during which the saliva sample is being collected and to analyze the saliva sample for the presence of drugs.

19. The method of claim 13, further comprising confirming that a the user is a pre-registered user.

20. The method of claim 13, wherein each sample collection device is preprinted with a unique barcode for tracking during further analysis.

* * * * *